(12) United States Patent
Davey et al.

(10) Patent No.: US 10,195,331 B2
(45) Date of Patent: Feb. 5, 2019

(54) HIGH FLOW RATE DIALYSIS CATHETERS AND RELATED METHODS

(71) Applicant: AngioDynamics, Inc., Latham, NY (US)

(72) Inventors: Christopher T. Davey, Boston, MA (US); Michael R. Sansoucy, Ayer, MA (US); Matthew N. McCarthy, Waltham, MA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 15/823,101

(22) Filed: Nov. 27, 2017

(65) Prior Publication Data

US 2018/0078693 A1 Mar. 22, 2018

Related U.S. Application Data

(60) Continuation of application No. 13/971,879, filed on Aug. 21, 2013, which is a continuation of application No. 12/166,962, filed on Jul. 2, 2008, now Pat. No. 8,540,663, which is a continuation of application No. 10/420,277, filed on Apr. 22, 2003, now Pat. No. 7,410,602, which is a division of application No. 09/859,090, filed on May 16, 2001, now Pat. No. 6,595,966, which is a continuation of application No. 09/256,421, filed on Feb. 23, 1999, now Pat. No. 6,280,423.

(60) Provisional application No. 60/075,724, filed on Feb. 24, 1998.

(51) Int. Cl.
*A61M 1/30* (2006.01)
*A61M 25/00* (2006.01)

(52) U.S. Cl.
CPC .......... *A61M 1/30* (2013.01); *A61M 25/0021* (2013.01); *A61M 25/0029* (2013.01); *A61M 25/0009* (2013.01); *A61M 2025/0031* (2013.01); *A61M 2025/0037* (2013.01)

(58) Field of Classification Search
CPC . A61M 25/0021; A61M 25/0029; A61M 1/30
See application file for complete search history.

(56) References Cited

U.S. PATENT DOCUMENTS 4,563,180 A * 1/1986 Jervis ................ A61M 25/0054
604/523
5,053,023 A * 10/1991 Martin ................ A61M 5/1582
604/43

* cited by examiner

*Primary Examiner* — Edelmira Bosques
(74) *Attorney, Agent, or Firm* — Zachary F. Madonna, Esq.

(57) ABSTRACT

High flow rate catheters, and related methods, are useful in dialysis and other procedures. A catheter according to the invention comprises a hub and a generally elongated conduit. The conduit has a substantially continuous and smooth wall. The conduit also defines at least one lumen and has a length extending from a proximal end to a distal end of the conduit. The proximal end is coupled to a hub and the distal end has an opening in communication with the lumen. The conduit has a conical shape which tapers along the length.

10 Claims, 10 Drawing Sheets

1 - 1'

1" - 1'''

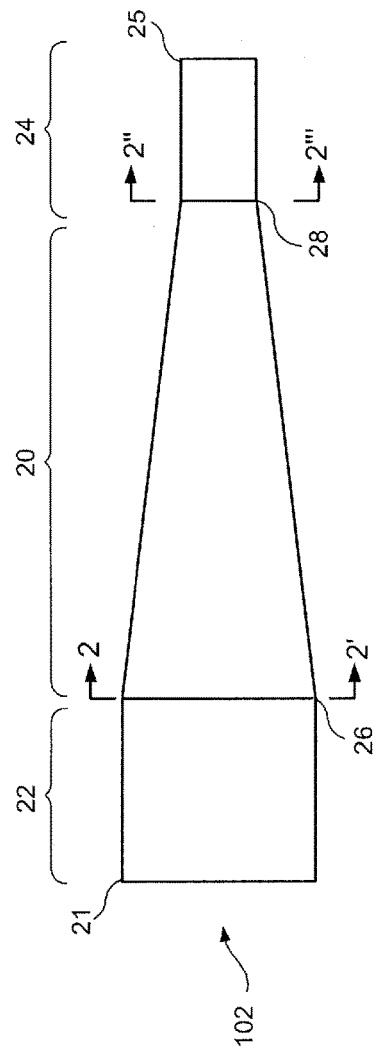
FIG. 2A
FIG. 2B
FIG. 2C

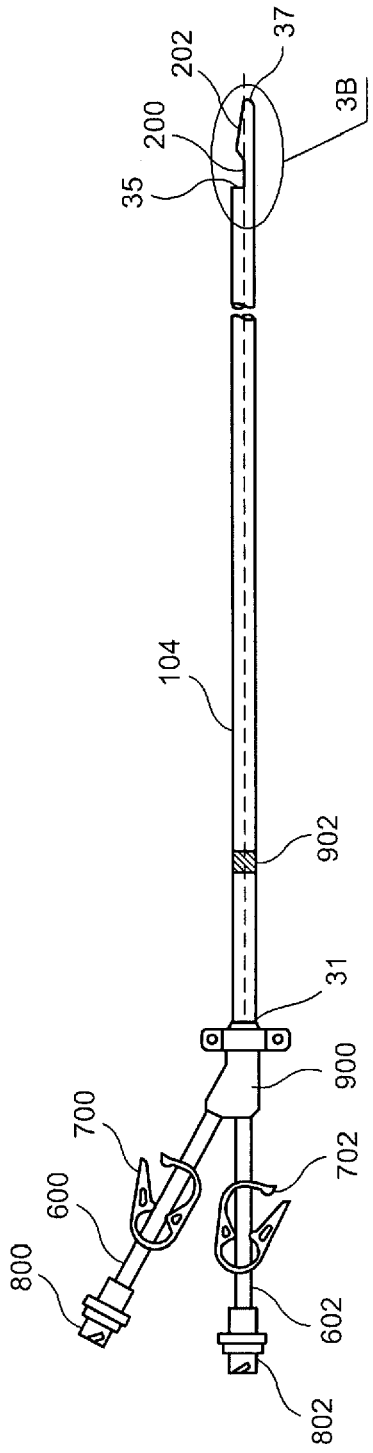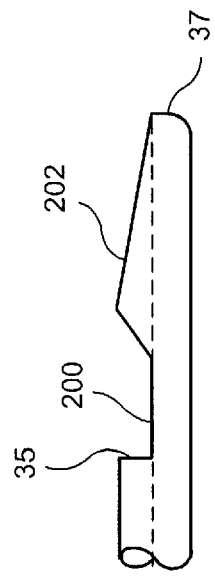
F I G. 3A
F I G. 3B

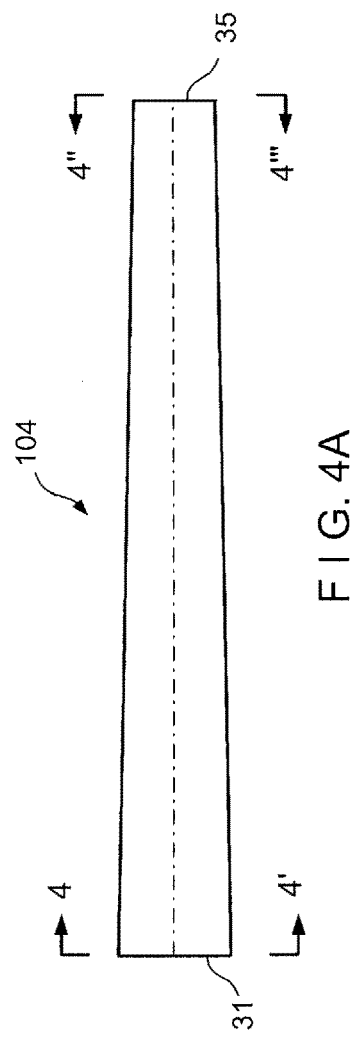
FIG. 4A
FIG. 4B
FIG. 4C

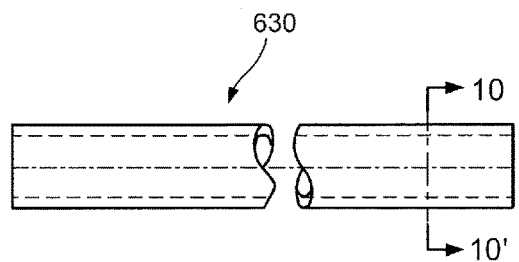
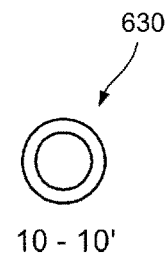
FIG. 10A
FIG. 10B
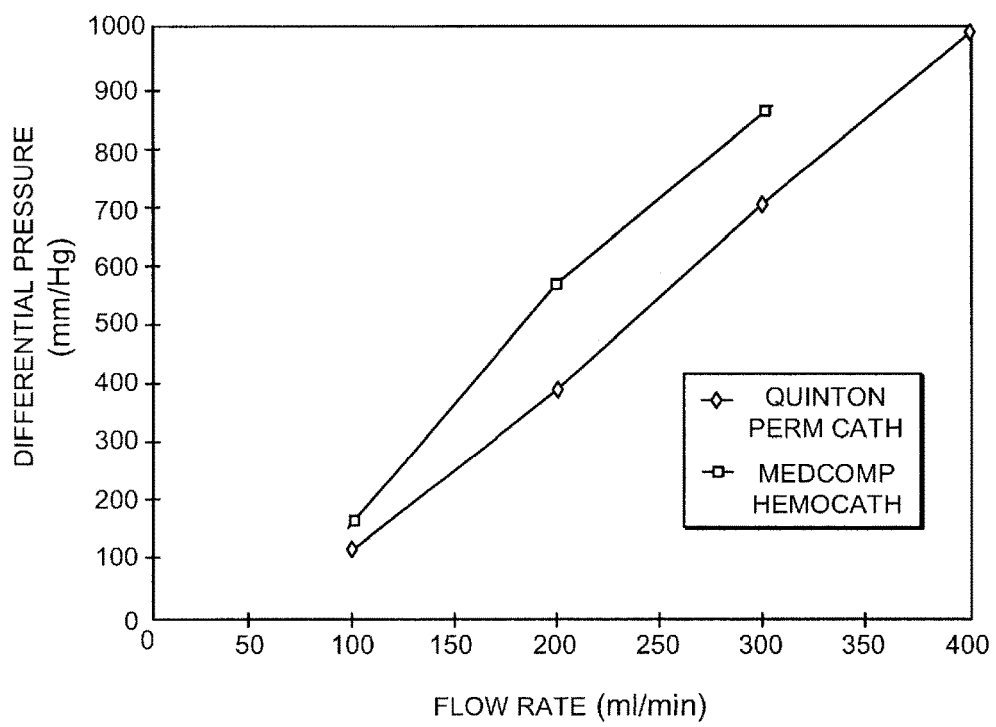
FIG. 11

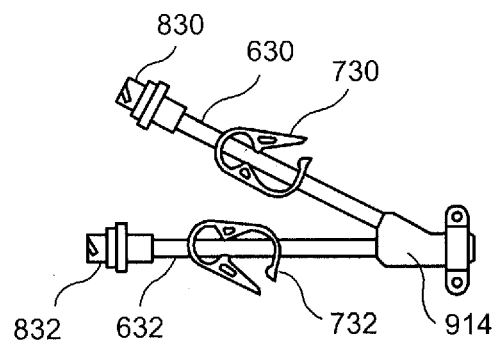
F I G. 13
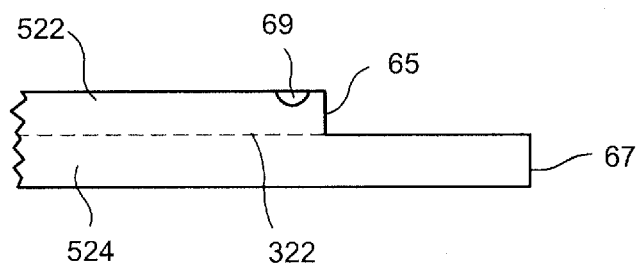
F I G. 14A
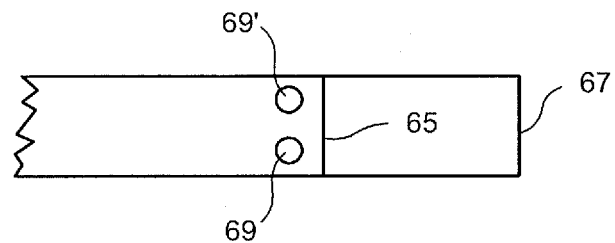
F I G. 14B

HIGH FLOW RATE DIALYSIS CATHETERS AND RELATED METHODS

CROSS-REFERENCE TO RELATED APPLICATION

This incorporates by reference, and claims priority to and the benefit of, U.S. provisional patent application Ser. No. 60/075,724 which was filed on Feb. 24, 1998.

TECHNICAL FIELD

This invention relates to catheter designs and methods of positioning and making catheter designs. More particularly, the invention relates to catheter designs that increase flow through a catheter as well as methods for positioning a catheter of these designs and making a catheter of these designs.

BACKGROUND OF THE INVENTION

Dialysis procedures, for example, frequently use dual lumen catheters to transport blood from a patient to a dialysis machine and then return processed blood back to the patient. See, e.g., McIntosh et al., JAMA 169(8): 137-38 (1959). Functionality, comfort, ease of manufacture, and ease of use are all important considerations for catheter designs. Specifically, high flow rates through catheters are necessary to maximize the efficiency of dialysis procedures. Both the physiology of blood and the designs of conventional catheters limit flow rate. Blood cells cannot survive high pressure differentials or excessive mechanical shear.

Conventional catheters have a design which, while useful, does not maximize flow rate within the bounds of these physiological constraints. Additionally, conventional catheter designs have several other disadvantages. First, an intake lumen positioned with a vessel often becomes suctioned against the vessel wall, reducing flow through the catheter. Second, a shaft of a conventional catheter is prone to kinking, again reducing flow. Third, an internal septum that divides multiple lumens within a catheter is prone to deflection due to pump pressure.

SUMMARY OF THE INVENTION

It has been discovered that one can maximize the flow rate though a catheter despite design constraints of maximal catheter outer diameter ("french size") and bounded allowable pressure drop. In catheter designs of the present invention, one can tailor a catheter's internal geometry, the thickness of a catheter's wall and internal divider, and/or the ability of a catheter's internal divider to resist flexure when exposed to a pressure gradient in order to reduce resistance to flow, reduce the catheter's tendency to kink, and maximize flow rate. These design concepts are applicable equally to single lumen catheters, dual lumen catheters, or multiple lumen catheters. Also, the presence of a particular tip geometry at the entrance to at least one lumen minimizes the catheter's tendency to become suctioned against the vessel wall and ensures high flow rate.

In one aspect, the invention relates to a catheter comprising a hub and a generally elongated conduit having a substantially continuous and smooth wall. The conduit defines at least one lumen and has a length extending from a proximal end to a distal end of the conduit. The proximal end is coupled to the hub and the distal end has an opening in communication with the lumen. The conduit is conical and tapered along its length from the hub to the opening. The substantially continuous and smooth conduit wall has no openings, apertures, holes, roughness, or indentations over substantially all of its length.

Embodiments of this aspect of the invention can include the following features. For example, the wall can have a notch distal to the distal end, and the notch can communicate with at least one of the lumens. The notch can comprise a longitudinal cut in the conduit. The notch can include a distal appendage. The notch can comprise an opening having an area greater than that of a transverse cross-sectional area of the conduit immediately proximal to the opening. In dual lumen embodiments, a first lumen may extend from the proximal end to the opening at the distal end and a second lumen may extend from the proximal end to a point distally beyond the opening which may have a second opening. Also, the conduit may be conical and tapered from the proximal end to the point distally beyond the opening.

The conduit wall can have a thickness greater at the proximal end than at the distal end, and the thickness of the wall can transition between the proximal end and the distal end. At least one of the lumens can increase in cross-sectional area from the distal end to the proximal end or a portion thereof. A surface of the conduit can be treated, with heparin, for example, to inhibit association of materials, including biological materials, with the conduit (e.g., inhibit deposit of materials on the surface and/or inhibit materials from surrounding the conduit). The conduit can be generally conical, and the conduit can be a truncated cone in shape.

A transverse cross-section of the conduit can be round or oval, for example. A transverse cross-section of at least one of the lumens can be circular or partly circular, for example. At least a portion of the conduit can be curved. At least a portion of the conduit can be reinforced with, for example, a fiber, a wire, a material that is harder than the conduit, and/or a material that is softer than the conduit. The conduit can further comprise at least one cuff. The conduit also can further comprise at least one internal divider defining at least two lumens.

The catheter can further comprise at least one connecting tube connected to the hub. At least one of the connecting tubes can be in communication with at least one of the lumens. At least one of the connecting tubes can be curved and oriented in parallel with a distal portion of the conduit, straight and oriented approximately 180 degrees from a distal portion of the conduit, or oriented somewhere between these two positions. One or more of the connecting tubes can be selectively removable (e.g., so that it can be replaced if damaged).

At least one of the internal dividers can have a thickness greater at the proximal end than at the distal end, and the thickness can transition between the proximal end and the distal end. At least a portion of one of the internal dividers can be reinforced with a material stiffer than the conduit. One or more of the internal dividers can be connected with the wall of the conduit distal to the notch.

In another aspect, catheters according to the invention comprise a hub and a flexible, generally elongated conduit having an outer wall and defining at least one lumen. The conduit comprises a proximal section extending from a proximal end, which is coupled to the hub, to a first point. The proximal section has a first cross-sectional area along its length. A middle section extends from the first point to a second point. The first cross-sectional area at the first point is larger than a second cross-sectional area at the second point. A distal section extends from the second point to a distal end. The distal section has the second cross-sectional area along its length. The thickness of the wall increases in a distal to proximal direction over at least a portion of the conduit. At least one lumen has a cross-sectional area that increases in a distal to proximal direction over at least a portion of the conduit. In certain embodiments, the thickness of the wall increases in thickness from the second point to the first point and the cross-sectional area of at least one lumen increases from the second point to the first point.

In certain embodiments, a surface of the conduit can be treated, with heparin, for example, to inhibit association of materials. including biological materials, with the conduit (e.g., inhibit deposit of materials on the surface and/or inhibit materials from surrounding the conduit). The conduit can further comprise at least one cuff. The conduit also can further comprise at least one internal divider defining at least two lumens. At least one of the internal dividers can have a thickness greater at the proximal end than at the distal end, and the thickness can transition between the proximal end and the distal end. A first lumen may extend from the proximal end to the opening at the distal end and a second lumen may extend from the proximal end to a point distally beyond the opening which may have a second opening. At least a portion of the conduit can be reinforced with, for example, a fiber, a wire, a material that is harder than the conduit, and/or a material that is softer than the conduit. The catheter can further comprise at least one connecting tube connected to the hub. At least one of the connecting tubes can be in communication with at least one of the lumens.

Methods of positioning or placing catheters according to the invention, as well as methods of making the catheters by extrusion, are described and constitute aspects of the invention. One method involves placing a catheter of the type described above by inserting it into a vessel having a breach and then positioning it within the vessel. Another method involves making a catheter of the type described above by extruding it into the desired shape such as a conical shape.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2A is a side view of another embodiment of a conduit of a catheter according to the invention.

FIG. 2B is a cross-section of the conduit of FIG. 2A taken along line 2-2'.

FIG. 2C is a cross-section of the conduit of FIG. 2A taken along line 2"-2'".

FIG. 3A is a side view of one embodiment of a catheter with a conical conduit.

FIG. 3B is an enlarged view of a notch and a distal appendage of the catheter of FIG. 3A.

FIG. 4A is a side view of one embodiment of the conduit of FIG. 3A produced by extrusion.

FIG. 4B is a cross-section of the conduit of FIG. 4A taken along line 4-4'.

FIG. 4C is a cross-section of the conduit of FIG. 4A taken along line 4"-4'".

FIG. 10A is a side view of one embodiment of a connector tube.

FIG. 10B is a cross-section of the connector tube of FIG. 10A taken along line 10-10'.

FIG. 11 is a graph showing a comparison of flow rate data on existing catheter designs.

FIG. 13 is a view of one embodiment of a hub assembly.

FIG. 14A is a side view of one embodiment of a tip configuration.

FIG. 14B is a top view of the embodiment of FIG. 14A which has been rotated 90 degrees.

DESCRIPTION

I. Introduction

Figure 1A:
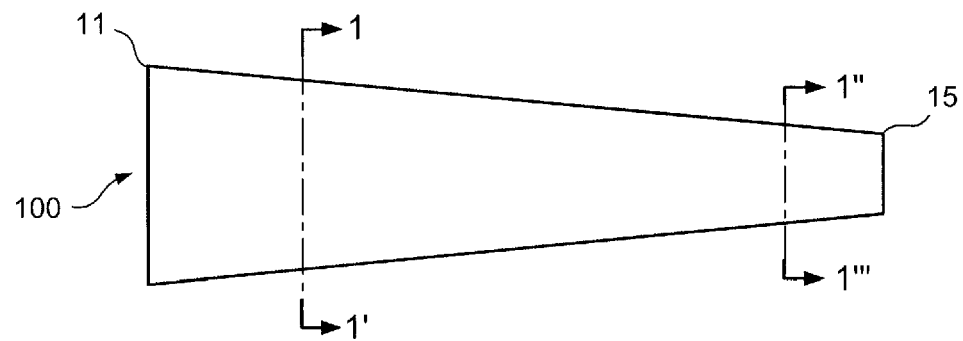
FIG. 1A is a side view of one embodiment of a conduit of a catheter according to the invention.
Figure 1B:
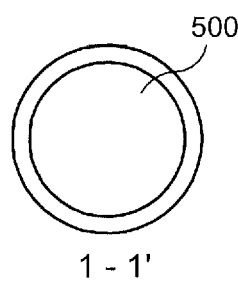
FIG. 1B is a cross-section of the conduit of FIG. 1A taken along line 1-1'.
Figure 1C:
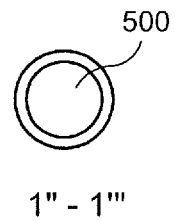
FIG. 1C is a cross-section of the conduit of FIG. 1A taken along line 1"-1'".

The present invention relates to catheters designed for high flow rates and to methods for positioning and making such catheters. The present invention minimizes the pressure drop across the length of a catheter, minimizes the shear imparted to blood cells traveling through it, and, thus, maximizes the flow rate through it. The designs and methods of the present invention apply equally to single lumen, double lumen, and multiple lumen embodiments. Moreover, the designs and methods of the present invention apply equally to all situations where flow rate (or any other similar measure) through a conduit needs to be increased and/or maximized.

Furthermore, during use, the entrance to a conventional catheter's suction lumen can become suctioned against the vessel wall, reducing the amount of blood which can enter the catheter and reducing flow. The present invention provides designs for a tip configuration which minimize the occurrence of this problem.

Additionally, if any section of a conventional catheter becomes kinked, the effective cross sectional area of at least one of the lumens is reduced and a reduction in flow rate through the catheter occurs. Kinking usually occurs in a tunneled section of a conventional catheter which follows a curved path between the venotomy and the catheter's percutaneous exit site. Kinking of conventional catheters is a problem because many of these catheters minimize wall thickness in order to maximize the lumen size (to, for example, attain a proper flow rate) while maintaining acceptable catheter french size (to, for example, allow the catheter to be placed comfortably into a patient). The present invention provides designs for a catheter's internal geometry as well as a catheter's wall thickness in order to achieve high flow rates without compromising effective clinical french size and in order to reduce the tendency of the catheter to kink.

Also, in conventional catheters, flow rate is reduced if the septum, or divider, that separates the lumen is too flexible. The septum deflects in the proximal portion of the catheter under the flow pressure differential created by the relatively high positive pressure in the discharge (venous) leg/lumen and the relatively low negative pressure created in the intake (arterial) leg/lumen. The deflection restricts flow. The need to maximize the cross sectional area of the lumens both by minimizing deflection and by minimizing septum thickness (i.e., maximizing lumen cross-sectional area) while maintaining acceptable french size constrains the thickness of the septum in current designs. The present invention provides for optimization of internal divider thickness in order to minimize septum flexibility under a pressure differential without compromising lumen cross-sectional area within the constraint of effective clinical french size.

Thus, the present invention provides new catheter designs that maximize flow rate through catheters according to three principles: (1) maximizing the catheter's internal volume to surface area ratio, (2) minimizing the potential for a suction lumen entrance to become suctioned against a vessel wall and, (3) minimizing the potential for kinking of the catheter shaft without adding wire reinforcement.

II. Lumen Cross-Sectional Area

Ohm's law describes the relationship amongst Flow Rate ("Q"), Pressure Drop (".DELTA.P"), and Resistance ("R") in catheters as follows.

$Q=.DELTA.P/R$ or $.DELTA.P=Q.times.R$

One option to increase flow-rate is to increase pump pressure (and hence increase .DELTA.P) in conjunction with existing catheters. This option is not practicable because increasing the pressure would destroy blood cells. The physiological limit of blood cells to withstand changes in pressure constrains .DELTA.P across the device. Thus, in order to increase Q, one must reduce R.

Increasing lumen size is one way to reduce R and generally has been explored. Catheters currently in use increased lumen size, but only within the constraint of an acceptable french size. The present invention moves beyond simply large lumens and further reduces the catheter's overall resistance to flow. Friction is the source of R. The two major sources of friction are the viscosity of the blood (i.e., friction generated as cells and molecules move in relation to each other) and the friction imparted by the walls of the catheter defining the lumen on the flow of blood. While varying blood viscosity generally is not an option, catheters of the present invention are designed so that the frictional effects of the catheter wall on the flow of blood are minimized, or at least reduced, over known designs.

In a two dimensional flow model, friction, and thus R, is reduced with an increasing ratio of lumen cross-sectional area to perimeter. A circular geometry provides the maximum ratio possible, which is why circular lumens have higher flow rates than semi-circular or non-circular lumens of equal area. In a three dimensional model, friction, and thus R, is reduced with an increasing ratio of lumen volume to lumen surface area. Maximizing this ratio in the present invention minimizes R and maximizes Q for any given .DELTA.P.

Referring to FIG. 11, the graph shows Q as a function of .DELTA.P for two existing dialysis catheters (Medcomp's "Hemocath" and Quinton's "Perm Cath"). The slope of the curve measures each device's R (shallower slope indicates less resistance). These catheters have essentially the same lumen cross-sectional areas. Both are silicone catheters. The primary difference between them is that the Perm Cath has two circular lumens and the Hemocath has one crescent shaped intake lumen and one circular lumen. The surface area of the intake lumen of the Hemocath is 35% greater than that of the Perm Cath. The cross-sectional areas and volumes of the lumens within these two catheter shafts are equal. The cross-sectional areas of the lumens are constant along their length for both catheters. Thus, the Perm Cath has a larger lumen volume to lumen surface area ratio than does Hemocath. The resistance to flow R, as indicated by the slope of the curves, is approximately 20% less for the Perm Cath. These data illustrate the benefits to flow rate of maximizing the ratio of lumen volume to surface area.

Embodiments of catheters of the present invention have lumens which grow in cross-sectional area along the length of the catheter conduit and through the hub and extension tube assemblies. Thus, embodiments of catheters of the present invention maximize the ratio of lumen volume to lumen surface area. Consequently, R is reduced and Q, flow rate, is increased. The increasing cross-sectional area further maximizes the ratio of lumen volume to lumen surface area regardless of whether the lumen is circular, semicircular, or non-circular.

In one embodiment of the present invention, a generally conical catheter conduit 100 tapers along its entire length from a proximal end 11 to a distal end 15 (FIG. 1A). In an alternative embodiment, a catheter conduit 102 is not a simple cylindrical shape, but is instead comprised of a frusto-conical middle section 20 bounded proximally at a first point 26 by a relatively large-diameter cylindrical proximal section 22 having a proximal end 21 and distally at a second point 28 by a relatively small-diameter cylindrical distal section 24 having a distal end 25 (FIG. 2A). In both of these embodiments, the cross-sectional area of the lumen 500, 502 taken along line 1-1' or 2-2' is larger than the cross-sectional area of the lumen 500, 502 taken along line 1"-1'" or 2"-2'" (FIGS. 1B, 1C and FIGS. 2B, 2C, respectively). Of course, a catheter conduit with any cross-sectional lumen area that increases or maximizes the lumen volume to lumen surface area ratio is a useful catheter design of the present invention.

Referring to FIG. 3A, in another embodiment, a conduit 104 is generally conical and tapered. The conduit 104 is substantially smooth and continuous with no holes, openings, apertures, roughness, or indentations over substantially all of its length. The entire length of the conduit 104 is 28 cm. The proximal end 31 couples to a hub 900 and a distal end 35 is immediately proximal to a notch 200. The conduit 104 comprises a width of 16F outer diameter at the proximal 31 and a width of 13F outer diameter at the distal end 35. The conduit 104 has a constant taper along its length from the proximal end 31 to the distal end 35. The conduit 104 extends beyond the distal end 35 to a notch 200, distal appendage 202, and, then, the physical end of the conduit 37. In alternative embodiments, the constant taper may extend distally beyond the distal end, for example, to the physical end of the conduit.

FIG. 4A shows a stylized side view of the embodiment of the conduit 104, excluding the portion of the conduit 104 which is distal to the distal end 35. The cross-section of the proximal end 31 taken along line 4-4' has a larger outer diameter french size (FIG. 4B) than the cross-section of the distal end 35 taken along line 4"-4'" (FIG. 4C). Moreover, the wall 400 at the proximal end 31 is thicker than the wall 402 at the distal end 35. The embodiment is shown with an internal divider 300, 302 that divides the internal space of the conduit 104 into two lumen 504, 506. Each of these two lumen 504, 506 connect with a corresponding connecting tube 600, 602 through the hub 900. Typically, the hub contains voids that link each of the lumens 504, 506 to one of the connecting tubes 600, 602.

Of course, a catheter conduit of the present invention need not have these exact measurements. Those skilled in the art are capable of constructing catheters of designs according to the present invention in any form suitable for a particular use. The skilled artisan need only apply the general principles of the present invention to a particular situation.

In some other embodiments of catheter designs of the invention, practical lumen geometries for achieving high flow dialysis are based on and can be calculated with the numerical dimensions provided in Table 1, below. In Table 1, "outer diameter" refers to the diameter of a conduit as measured from outermost point of an outer wall to outermost point of an outer wall; "width" refers to the diameter of a conduit as measured from innermost point of an outer wall to an innermost point of an outer wall; "height" refers to a radius of a conduit as measured from an internal divider, and in a perpendicular orientation to the internal divider, to the innermost point of an outer wall; "internal divider" refers to the thickness of an internal divider; "outer wall" refers to the thickness of an outer wall; the distal section refers to a portion of the conduit that is generally towards the tip of the conduit; and the proximal section refers to a portion of the conduit that is generally towards the hub. For example, Table 1 is useful to calculate lumen volumes, lumen surface areas, and other physical attributes of the depicted conical conduit design.

outer diameter at the distal end 45. Sections of the conduit 106 taken along lines 5-5' and 5"-5'" reveal that the more proximal locus (5-5', FIG. 5B) has a thicker wall 410 and a thicker internal divider 310 than the more distal locus (5"-5'", FIG. 5C) with a wall 412 and an internal divider 312. The internal divider 310, 312 divides the internal space of the conduit 106 into two lumens 508, 510. Each of these two lumens 508, 510 connect with a corresponding connecting tube 610, 612 through the hub 904. Typically, the hub contains voids that link each of the lumens 508, 510 to one of the connecting tubes 600, 602.

Of course, a catheter conduit of the present invention need not have these exact measurements. Those skilled in the art are capable of constructing catheter designs according to the present invention in any form suitable for a particular use. The skilled artisan need only apply the general principles of the present invention to a particular situation.

In some other embodiments of catheter designs of the invention, practical lumen geometries for achieving high flow dialysis are based on and can be calculated with the numerical dimensions provided in Tables 2 and 3, below. In Table 2, "outer diameter" refers to the diameter of a conduit as measured from outermost point of an outer wall to outermost point of an outer wall; "width" refers to the diameter of a conduit as measured from innermost point of an outer wall to innermost point of an outer wall; "height" refers to the radius of a conduit as measured from an internal divider, and in a perpendicular orientation to the internal divider, to the innermost point of an outer wall; "internal divider" refers to the thickness of an internal divider; "outer wall" refers to the thickness of an outer wall. In Table 3 "proximal section length" refers to the length of a proximal section as measured from a proximal end to a first point;

TABLE 1

CONICAL DESIGN CONDUIT (13-16F/28 ± 1.5 CM LENGTH)

| SECTION OF CONDUIT | OUTER DIAMETER (IN) | WIDTH (IN) | HEIGHT (IN) | INTERNAL DIVIDER (IN) | OUTER WALL (IN) |
| --- | --- | --- | --- | --- | --- |
| DISTAL | .170 ± .005 | .134 ± .005 | .060 MIN | .008 MIN | .013 MIN |
| PROXIMAL | .210 ± .005 | .143 MIN | .068 MIN | .009 MIN | .021 MIN |

Figure 5A:
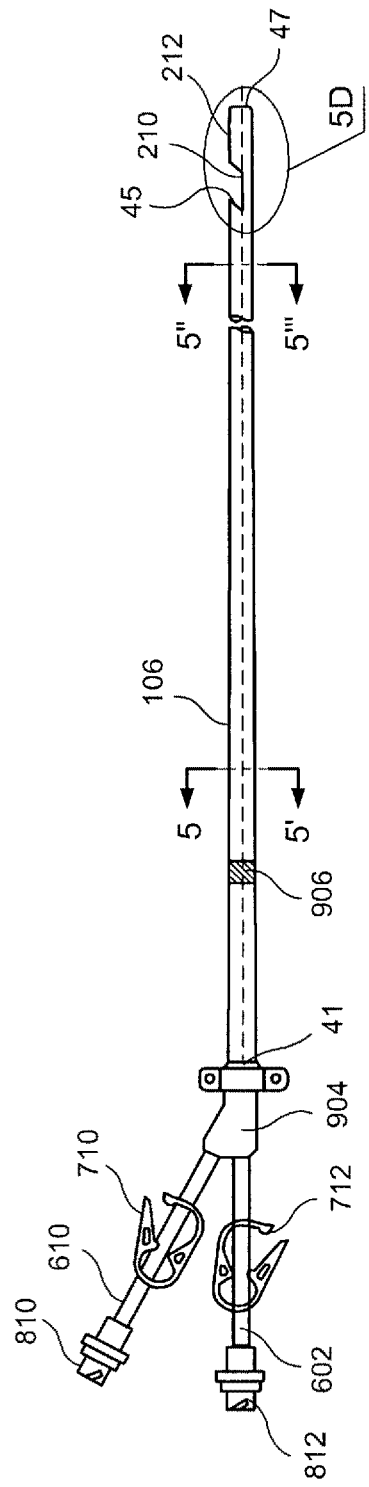
FIG. 5A is a side view of one embodiment of a catheter with a conduit having a cylindrical proximal section, a frusto-conical middle section, and a cylindrical distal section.
Figure 6:
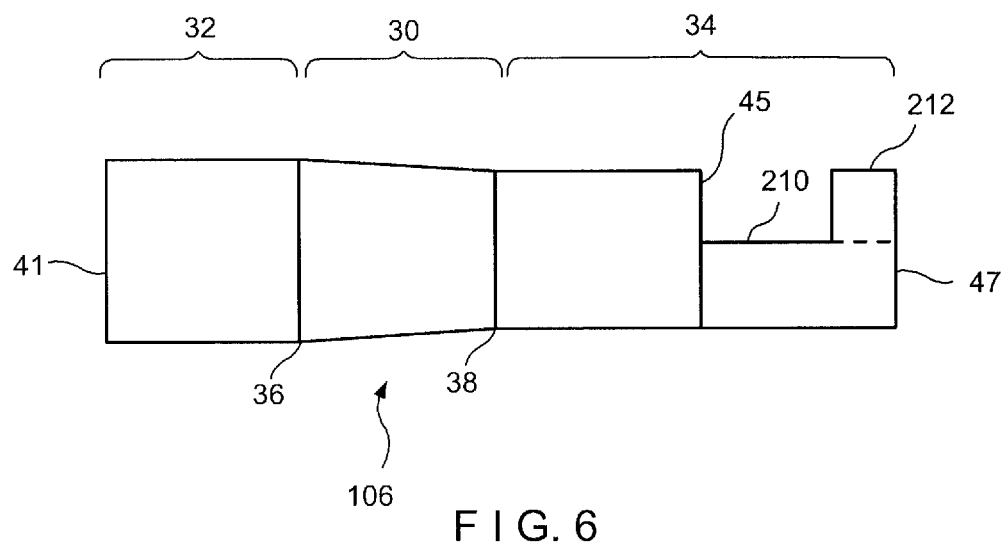
FIG. 6 is a stylized side view of one embodiment of the conduit of FIG. 5A produced by extrusion.

Referring to FIGS. 5A and 6, in another embodiment, a conduit 106 has a cylindrical proximal section 32 extending from a first point 36 to a proximal end 41 which is coupled to a hub 904, a frusto-conical middle section 30, and a cylindrical distal section 34 extending from a second point 38 to a distal end 45, notch 210, distal appendage 212, and, finally, the physical end of the conduit 47. The entire length of the conduit 106 is 28 cm and comprises a width of 15F outer diameter at the proximal end 41 and a width of 13F "middle section length" refers to the length of a middle section as measured from a first point to a second point; and "distal section length" refers to the length of a distal section as measured from a second point to a distal end. For example, Tables 2 and 3 are useful to calculate lumen volumes, lumen surface areas, and other physical attributes of the depicted cylindrical/frusto-conical/cylindrical conduit design.

TABLE 2

CYLINDRICAL/FRUSTO-CONICAL/CYLINDRICAL DESIGN CONDUIT (13-15F)

| SECTION OF CONDUIT | OUTER DIAMETER (IN) | WIDTH (IN) | HEIGHT (IN) | INTERNAL DIVIDER (IN) | OUTER WALL (IN) |
| --- | --- | --- | --- | --- | --- |
| DISTAL | .170 ± .005 | .134 ± .005 | .065 ± .003 MIN | .008 MIN | .013 MIN |
| PROXIMAL | .197 ± .005 | .143 MIN | .068 MIN | .009 MIN | .021 MIN |

TABLE 3

CYLINDRICAL/FRUSTO-CONICAL/CYLINDRICAL DESIGN
CONDUIT SECTION LENGTHS

| PROXIMAL SECTION LENGTH (CM) | MIDDLE SECTION LENGTH (CM) | DISTAL SECTION LENGTH (CM) |
|---|---|---|
| 16.0 MIN | 5.0 ± 1.5 | 16.0 MIN |

III. Tip Design

Figure 5D:
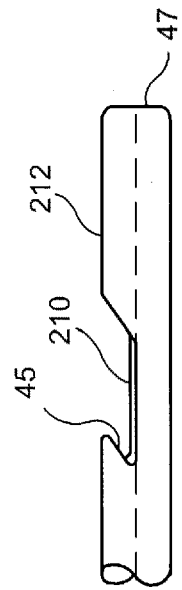
FIG. 5D is an enlarged view of a notch and a distal appendage of the catheter of FIG. 5A.

Catheter designs of the present invention provide for tip designs of a catheter that minimize the possibility of restricted flow into the catheter due to contact between a catheter and a vessel. Referring to FIGS. 3A and 3B, an embodiment of the invention is shown with a tip configuration. This configuration includes a "fin-shaped" distal appendage 202 between a notch 200 and the physical end of the conduit 37. Referring to FIGS. 5A and 5D, another embodiment of the invention is shown with another tip configuration. This embodiment also includes a "trapezoidal" distal appendage 212 between a notch 210 and the physical end of the conduit 47.

Figure 9:
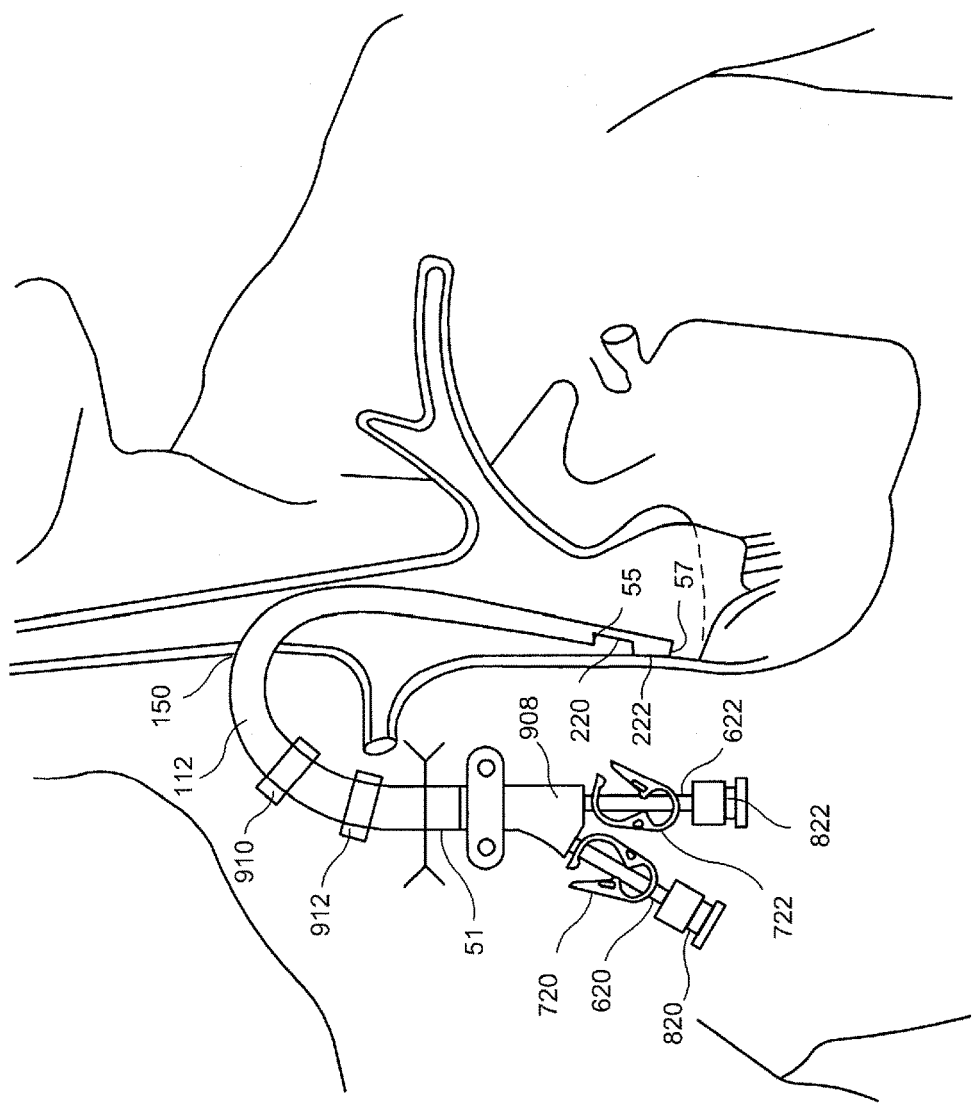
FIG. 9 is a view of one embodiment of a catheter placed within a vessel.
Figure 12:
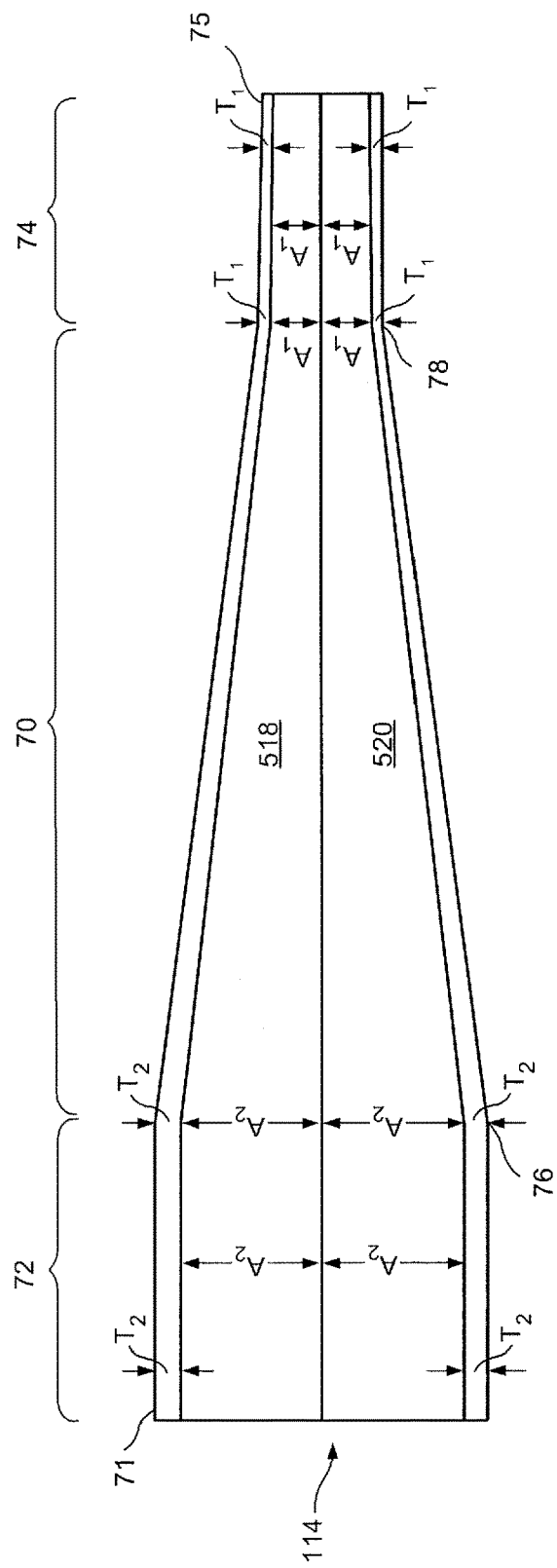
FIG. 12 is a sectional view along the length of one embodiment of a conduit.

FIG. 9 shows another embodiment of the invention with a tip configuration including a distal appendage 222 between a notch 220 and the physical end of the conduit 57 that is positioned against a vessel wall. Note that the distal appendage 222 of the invention prevents the catheter inlet from coming into direct contact with the vessel, reducing the likelihood that the vessel will impede flow into the catheter.

In another embodiment of the invention, the tip configuration comprises an internal divider which is attached to an inside surface of a lumen wall (e.g., an intake lumen) distal of a notch. This arrangement accomplishes two things: (1) it closes off the dead lumen space distal of the notch and (2) it expands the cross-sectional area of a second lumen (e.g., a discharge lumen) distal of the notch.

Referring to FIGS. 14A and 14B, another embodiment of a tip configuration does not have a notch or a distal appendage. The tip encloses two lumens 522, 524 defined by an internal divider 322 which terminate at openings at the distal end 65 and at the physical end of the conduit 67, respectively. Holes 69, 69' in the wall of the conduit immediately proximal to the distal end 65 communicate with the lumen 522. The holes 69, 69' are useful, for example, as an alternative fluid intake location if the distal end 65 becomes suctioned against a vessel wall. Alternative embodiments may have multiple holes positioned immediately proximal to the distal end of a conduit.

IV. Resistance to Kinking

Figures 5B, 5C:
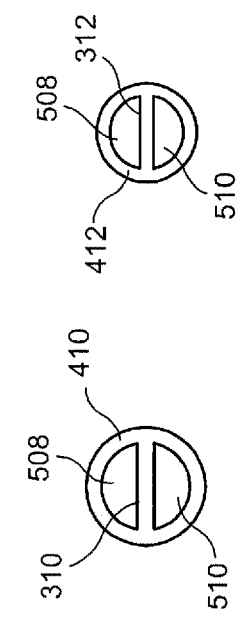
FIG. 5B is a cross-section of the conduit of FIG. 5A taken along line 5-5'.
FIG. 5C is a cross-section of the conduit of FIG. 5A taken along line 5"-5'".

The present invention provides for catheter designs which reduce the likelihood of conduit kinking and, thus, reduce the likelihood of reduction of flow rate through a catheter. FIGS. 5B and 5C show cross-sections of one embodiment of a conduit 106 at points 5-5' (towards the proximal end 41 of the conduit 106) and 5"-5'" (towards the distal end 45 of the conduit 106), respectively. A wall 410 of the conduit 106 at point 5-5' (FIG. 5B) is thicker than a more distally located wall 412 of the conduit 106 at point 5"-5" (FIG. 5C). Thus, the wall of the conduit 106 thins in a distal direction along its length. This change in thickness of the wall has two advantages. First a significant increase in the wall thickness in a proximal section reduces the conduit's tendency to kink when curved. Second, the reduced thickness in a distal section allows the lumen cross sectional area to be increased. Of course, other embodiments of the invention, such as catheters with conduits conical along their length from a hub to an opening or to the conduit end, may also have this change in wall thickness from proximal and to distal end.

Referring again to FIG. 9, note that, in this embodiment of the invention, a section of conduit 112, distal to a venotomy 150, hangs in a relatively straight fashion inside a vessel, and that a section of conduit 112, proximal to the venotomy 150 (within the tunnel), is sharply curved. The tunnel is the path within the body that a catheter takes, such as, from a point of entry into the body, through an area between the skin and the underlying facia layer, to a point of entry into a vessel. Cuffs 910, 912 assist with proper placement and retention of the catheter.

The physician or other device operator inserts the catheter into the body at the point of entry, tunnels through the body tissue to the site of a breach in a vessel wall, and advances the catheter through the breach such that at least a portion of the catheter is positioned within the vessel. Commonly, a catheter is inserted into and through a portion of the Internal Jugular Vein. Often a catheter tip is positioned at the Superior Vena Cava and/or the right atrial junction. However, a catheter of the present invention is useful in any vessel that accommodates the size of the catheter (e.g., inserting the catheter into and through a portion of the femoral vein and positioning a tip of the catheter in the Vena Cava). The thicker wall of this embodiment of the invention allows a more acute curvature of the conduit 112 without kinking than does a conventional catheter. Thus, the physician or other device operator has more options when selecting the tunnel path than with conventional catheters because the catheter of this embodiment of the invention is capable of a greater range of motion than conventional catheters. Moreover, the physician or other device operator can take into account other considerations such as patient comfort, appearance, and the presence of other devices when positioning the device.

Also, FIG. 9 shows this embodiment of the catheter with two connector tubes 620, 622. Each connecting tube 620, 622 has a clamp 720, 722 and a Luer fitting 820, 822 which allow the dialysis procedure to be undertaken efficiently. At least one of these connecting tubes 620, 622 is connected to a dialysis pump which assists in moving blood through dialysis machinery. The connecting tubes 620, 622 also connect with a corresponding lumen through the hub 908. The thicker conduit wall of this embodiment is more resistant to collapse from the suction of the dialysis pump.

V. Internal Divider Thickness

Referring again to the embodiment of the invention shown in FIGS. 5B and 5C, an internal divider 310 of a conduit 106 at one locus (FIG. 5B) is thicker than a more distally located internal divider 312 of the conduit 106 at a second locus (FIG. 5C). Thus, the internal divider within the conduit 106 thins in a distal direction along its length. Thickness of the internal divider is tapered so that it is thicker in a section of conduit closer to the proximal end 41 than it is in a section of conduit closer to the distal end 45. This change in thickness may be accomplished without reducing the cross-section of the lumen and thus restricting flow. The added thickness enables the internal divider in the proximal section to remain fixed in position when exposed to high differential pressures exerted in this region during dialysis or other procedures. Of course other embodiments of the invention, such as catheters with conduits conical along their length from a hub to an opening or to the conduit end, may also have this change in internal divider thickness from proximal end to distal end.

VI. Cylindrical Versus Conical Designs

Achievement of high flow rates is a key performance attribute for dialysis catheters. Blood viscosity and ability of cells to survive large pressure drops are non-controllable factors in the dialysis flow equation. Those controllable factors which are most relevant to maximizing flow rate through catheters include catheter french size (which dictates available lumen sizes), catheter length (shorter is better because shorter lumens have less surface area to cause friction), and catheter resistance to kinking (kinks restrict flow). Because the user of the catheter positions the device percutaneously, a compact, round catheter conduit is desirable in order to minimize the size of a venotomy and maximize patient comfort/acceptance of the device. Conventional catheters address these needs through purely cylindrical shafts. One embodiment of the present invention provides catheter designs with conical or generally conical conduits that have the same desirable features as cylindrical shafts. For example, often, during placement, a catheter is twisted. A round cross-section conduit may be twisted in a breach in a vessel without enlarging the breach. In contrast, a non-round cross-section conduit enlarges the breach when twisted, preventing the breach from sealing around the conduit properly.

Additionally, catheters of the invention with conical or generally conical conduits have other advantages that purely cylindrical shafts cannot achieve. For example, higher flow rates may be achieved because larger lumen volumes may be designed into a proximal section of conduit (i.e., a section of conduit adjacent to a hub). Also, thicker walls may be designed into a proximal section of the conduit which reduces the tendency of the conduit to kink. Moreover, the final size of the breach in a vessel is determined by a peelable sheath. The sheath normally is inserted into the breach and a catheter is subsequently inserted through the sheath. The sheath is peeled away once the catheter is inserted. Because a distal section of conduit of the present invention (i.e., a section of conduit towards the terminal end and/or tip of the catheter) may be smaller than conventional catheters with lower flow rates, smaller sheaths may be used (such that smaller breaches are necessary). Less area is needed to insert the smaller distal section through the breach, easing placement of a catheter. Furthermore, conical or generally conical designs are safer than purely conical designs because, as the catheter is advanced through the breach, the increasing cross-sectional area of the conduit seals the breach. In current catheter designs, the site of the breach must be manually compressed around the catheter until coagulation occurs. Thus, one can advance a conical catheter immediately after placement to fill up the annular space in the venotomy.

Figure 7:
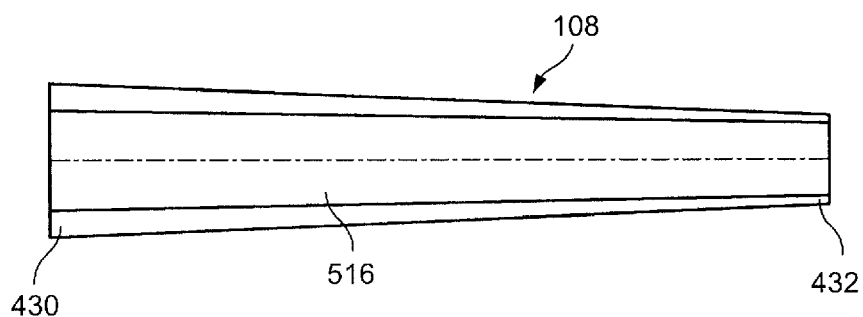
FIG. 7 is a section taken along the length of one embodiment of a conical conduit.
Figure 8:
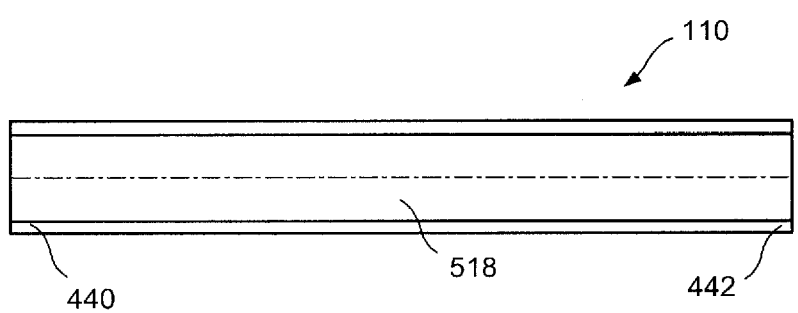
FIG. 8 is a section taken along the length of a cylindrical conduit.

Additionally, a conical conduit is a more efficient geometry for maximizing flow in a dialysis catheter than a purely cylindrical catheter. FIG. 7 shows a conical conduit 108 of one embodiment of the invention. FIG. 8 shows a cylindrical conduit 110, equal in length to the conduit 108 of FIG. 7. Each conduit 108, 110 has a lumen 516, 518 (FIGS. 7 and 8, respectively). Note also that wall thickness 432, 430, respectively, increases from distal end to proximal end of the conduit 108 of the embodiment shown in FIG. 7 while wall thickness 442, 440 remains constant along the length of the conduit 110 shown in FIG. 8. A smaller end of the conical conduit 108 has an inner diameter (i.e., measured from inner wall to inner wall) equal to that of the cylindrical conduit 110. For example, in a hypothetical situation, the inner diameter at the smaller end of the conical conduit 108 is equal to the diameter of the cylindrical conduit 110. 2 units in this case. The inner diameter of a larger end of the conical conduit 108 is 3 units. The length of both conduits 108, 110 is 10 units. The lumen volume (V), surface area (SA), and ratio of volume to surface area, (V/SA) is calculated according to standard geometric principles based on the given dimensions. Thus, the lumen volume, surface area, and ratio of volume to surface area is 49.74 units.sup.3, 78.64 units.sup.2, and 0.63 units, respectively, for the conical conduit 108. The lumen volume, surface area, and ratio of volume to surface area is 31.42 units.sup.3, 62.83 units.sup.2, and 0.50 units respectively for the cylindrical conduit 110. The V/SA for the conical conduit is greater than that of the cylindrical conduit. This result will always be true if the smaller end of a conical conduit has an inner diameter equal to or greater than that of a cylindrical conduit and if the conduits are of equal length.

Maximizing this ratio for lumens of a given minimum diameter and given length is a significant factor in improving flow through the device. The larger the ratio, the less resistance through the conduit, the greater the flow rate the device achieves. At the maximum pressure blood can tolerate, more flow will occur through the conical conduit than through the cylindrical conduit because at any given point in time a lower proportion of blood within the conical lumen is in contact with the surface of the lumen. Moreover, the increase in area allows a larger percentage of fluid to pass by without contact with the wall, decreasing the resistance to flow through the device.

Wall thickness of cylindrical conduits, at any point, cannot increase without a reduction in lumen cross-sectional area and an increase in resistance to flow. Both wall thickness and cross-sectional area can increase from a distal (near the tip) to proximal (near the hub) end in a conical or generally conical conduit. A proximal section of the catheter typically is curved as it passes through the subcutaneous tunnel. A distal section of the catheter hangs straight in the Vena Cava. Wall thickness is minimized in order to maximize lumen cross sectional area and minimize venotomy size. The increased wall thickness allows the catheter to have greater resistance to kinking and decreases the tendency for a catheter to kink when bent or curved. Kinking invariably restricts flow. Thus, the absence of kinking also adds to increased flow.

Conical or generally conical catheters are extrudable. Generally, a material which forms the conduit is placed in a device. This material often is heated and forced through a die. As the material is moving through the die, a pressurized gas, such as air, is introduced which forms one or more lumen. Additionally, as the material is forced through the die the extruded material is pulled from the leading end. Often the material is cooled as it is pulled. Thus, this extrusion system has at least three variables that effect the extruded product: the manner in which the material is forced through the die (e.g., the force applied and/or the rate of extrusion), the manner in which gas is introduced (e.g., the pressure of the gas or the length of application) and the manner in which the material is pulled (e.g., the rate at which the material is pulled). If these variables are held constant over time and the extruded tube is pulled at the same rate as it is extruded, a uniform tube is produced. Mismatching the rate of extrusion and the rate of pulling and/or altering these variables over time produces a non-uniform conduit, including designs of the present invention.

VII. Dual Lumen Catheters

In one embodiment of the invention the catheter comprises a conduit which is conical and tapered along its length from a proximal end to a distal end. The conduit is substantially continuous and smooth, having no openings, holes, apertures, roughness, or indentations over substantially all of its length. The embodiment has an internal divider and a conduit wall which define two lumens. The catheter is structured such that at least one lumen is tapered along its length. The tapered conduit as well as the tapered lumen are substantially larger in cross-sectional area at the proximal end than the distal end. The proximal end of the conduit couples with a hub. In turn, the hub connects with connecting tubes on the proximal side of the hub. Each of the two lumens connects with a corresponding connecting tube through the hub. Typically, the hub contains voids that link each of the lumens to one of the connecting tubes.

For example, FIG. 3A shows two connecting tubes 600, 602, each of which communicates with a different one of the lumens through a hub 900. Each connecting tube 600, 602 has a clamp 700, 702 which may be actuated to restrict or prevent flow through the connecting tubes 600, 602, and a Luer fitting 800, 802 which many be used for connecting other tubing (to a dialysis pump, for example). A cuff 902 is included for proper positioning and operation of the catheter. FIG. 10A shows a side view of one embodiment of a connecting tube 630 while FIG. 10B shows a cross-sectional view of the same connecting tube 630. One of the tapered lumens terminates at the distal end 35 such that it is in communication with the environment outside of the catheter via an opening at the distal end 35 and via a more distally located notch 200 in a wall of the elongated tapered conduit 104. The notch 200 has an area greater than the area of the transverse cross-sectional area of that lumen immediately proximal to the notch 200. The other tapered lumen terminates at the physical end of the conduit 37 and opposite the connecting tubes 600, 602 such that this lumen is in communication with the environment outside of the catheter.

This dual lumen, conical conduit embodiment of catheter designs of the invention includes the following features, either alone or in combination. A notch comprises a longitudinal cut in a wall of the catheter. A transverse cross-section of a conduit is round or oval. A transverse cross-section of a lumen is circular or partly circular (e.g., semi-circular). An outside wall at a proximal end of the conduit has a maximum thickness that tapers to a lesser thickness at a distal end of the conduit. An internal divider at a proximal end of the conduit is at a maximum thickness that tapers to a lesser thickness at a distal end of the conduit. A proximal section and/or a middle section of the conduit, closer to connecting tubes, comprises a curved portion. Connecting tubes are straight or curved and oriented such that they point away from a distal end of the conduit, are in parallel with a distal section, or are oriented between these two positions. A proximal, middle and/or distal section of the conduit is circumferentially reinforced with a fiber, a wire, a layer of material which is harder than the conduit material, and/or a layer of material which is softer than the conduit material. An internal divider is reinforced with a material generally stiffer than that of a wall of the conduit to minimize the tendency to deflect under pressure. A connector tube is selectively removable such that the connector tube is replaceable while the catheter is positioned within the patient. At least one cuff is included on a conduit for proper placement and operation of the invention.

Other desirable aspects of this dual lumen, conical embodiment of catheter designs of the invention as well as other possible embodiments of the present invention also may include the following features. A surface of a conduit is treated to affect the ability of bodily fluids (e.g., blood) to associate materials, such as biological materials, with the conduit (e.g., affect the ability of material to deposit on the surface of the conduit and/or affect the ability of materials to surround the conduit). For example, the outside surface is coated with an anticoagulant such as heparin. The use of heparin to treat surfaces is known in the art and is described, for example, in Riesenfeld et al., MEDICAL DEVICE TECHNOLOGY (March 1995), which is incorporated herein by reference.

In another embodiment of the invention a catheter comprises a conduit and an internal divider defining two lumens. The catheter comprises three sections, a proximal section, a middle section, and a distal section. The proximal section is cylindrical with a larger cross-sectional area than the cylindrical distal section. The proximal and distal sections flank a frusto-conical middle section. At least one internal divider and walls of the three sections define the lumens. The sizes of the lumens generally are proportional to the sizes of the sections. The end of the proximal section of the conduit (i.e., the proximal end) couples with a hub. In turn, the hub connects with connecting tubes on the proximal side of the hub. Each of the two lumens connects with a corresponding connecting tube through the hub. Typically, the hub contains voids that link each of the lumens to one of the connecting tubes.

For example, FIG. 5A shows two connecting tubes 610, 612, each of which communicates with a different one of the lumens through a hub 904. Each connecting tube 610, 612 has a clamp 710, 712, which may be actuated to restrict or prevent flow through the connecting tubes 610, 612, and a Luer fitting 810, 812 which may be used for connecting other tubing (to a dialysis pump, for example). A cuff 906 is included for proper positioning and operation of the catheter. One of the tapered lumens terminates at the distal end 45 such that it is in communication with the environment outside of the catheter via an opening at the distal end 45 and via a more distally located notch 210 in a wall of the elongated tapered conduit 106. The notch 210 has an area greater than the area of the transverse cross-sectional area of that lumen immediately proximal to the notch 210. The other tapered lumen terminates at the physical end of the conduit 47 and opposite the connecting tubes 610, 612 such that this lumen is in communication with the environment outside of the catheter.

This dual lumen, cylindrical/frusto-conical/cylindrical shaped conduit embodiment of catheter designs of the invention, includes the following features, either alone or in combination. A notch comprises a longitudinal cut in a wall of a conduit. A transverse cross-section of a connecting tube is round or oval. A transverse cross-section of a lumen is circular or partly circular (e.g., semi-circular). An outside wall at a proximal end of a conduit has a maximum thickness and has a lesser thickness at a distal end of the conduit. An internal divider at a proximal end of a conduit is at a maximum thickness that tapers to a lesser thickness at the distal end of the conduit. A proximal section and/or a middle section of the conduit, closer to connecting tubes, comprises a curved portion. Connecting tubes are straight or curved and oriented such that they point away from a distal terminating end of the conduit, are in parallel with a distal section, or are oriented between these two positions. A proximal, middle, and/or distal section of a conduit is circumferentially reinforced with a fiber, a wire, a layer of material which is harder than the conduit material, and/or a layer of material which is softer than the conduit material. An internal divider is reinforced with a material generally stiffer than that of a wall of a conduit to minimize the tendency to deflect under pressure. A connector tube is selectively removable such that the connector tube is replaceable while the catheter is positioned within the patient. At least one cuff is included on a conduit for proper placement and operation of the invention.

Other desirable aspects of this dual lumen embodiment of catheter designs of the invention as well as other possible embodiments of the present invention also include the following features. A surface of a conduit is treated to affect the ability of bodily fluids (e.g., blood) to associate materials, such as biological materials, with the conduit (e.g., affect the ability of material to deposit on the surface of the conduit and/or affect the ability of materials to surround the conduit). For example, the outside surface is coated with an anticoagulant such as heparin. The use of heparin to treat surfaces is known in the art and is described, for example, in Riesenfeld et al., MEDICAL DEVICE TECHNOLOGY (March 1995), which is incorporated herein by reference.

Referring to FIGS. 13 and 14, another embodiment of the invention has a hub 914 and flexible, generally elongated conduit 108 defining at least one lumen 518, 520. The conduit 108 has a proximal end 71 which is coupled to the hub 914. From the proximal end 71, the conduit 108 extends distally to a first point 76. The proximal end 71 and the first point 76 define a cylindrical proximal section 72 of the conduit 108. From the first point 76, the conduit 108 extends to a second point 78. The first point 76 and the second point 78 define a middle section 70. The middle section 70 has a frusto-conical shape with a larger cross-sectional area at the first point 76 than at the second point 78. From the second point 78, the conduit 108 extends to a distal end 75 having an opening. The opening communicates with at least one lumen 518, 520. The second point 78 and the distal end 75 define a cylindrical distal section 74.

The proximal section 72 has a constant cross-sectional area along its length which is the same as the cross-sectional area at the first point 76. The distal section 74 has a constant cross-sectional area which is the same as the cross-sectional area at the second point 78. The conduit wall of the distal section 75 has a constant thickness $T_1$ along its length. This thickness $T_1$ increases proximally, through the middle section 70, to a larger thickness $T_2$ at the first point 76. Thus, the thickness of the conduit wall $T_2$ at the first point 76 is greater than the thickness of the conduit wall $T_1$ at the second point 78. The conduit wall of the proximal section 72 has a constant thickness $T_2$ along its length which is the same thickness $T_2$ as at the first point 76.

At least one of the lumens 518, 520 has a constant inner diameter $A_1$ measured from the internal divider to the wall along the length of the distal section 74. This inner diameter $A_1$ grows proximally along the length of the middle section 70 to the first point 76 where it reaches an inner diameter of $A_2$. The inner diameter of the lumen $A_2$ remains constant along the length of the proximal section 72 and is the same inner diameter $A_2$ as that at the first point 76. Thus, the inner diameter $A_2$ at the first point 76 is larger than the inner diameter $A_1$ at the second point 78. Simple geometric principles can be used to convert inner diameters to cross-sectional areas, depending upon the shape of the lumen 518, 520 cross-section. Thus, a cross-sectional area calculated from $A_2$ is larger than a cross-sectional area calculated from $A_1$. In fact, as the inner diameter increases through the middle section 70 of this embodiment, the cross-sectional area of each lumen 518, 520 also increases correspondingly.

At the proximal end 71, the conduit 108 couples to the hub 914 such that at least one of the lumens 518, 520 communicates with a void within the hub 914. Preferably, each lumen 518, 520 communicates with a different void. On the side of the hub 914 opposite from the conduit 108, at least one, and preferably two, connecting tubes 630, 632 connect with each void in the hub 914. Thus, in this embodiment each of the two lumens 518, 520 are in communication with each of the two connecting tubes 630, 632 through voids in hub 914. Each of the connecting tubes 630, 632 have Luer fittings 830, 832 on the end to connect to other tubing and/or devices (such as a dialysis pump) and have a clamp 730, 732 which can be actuated to restrict or prevent flow through the particular connecting tube 630, 632. Also, a cuff (not shown in this embodiment but similar to cuff 906 of FIG. 5A) is provided around the outside of the conduit 108. The cuff is a porous material which allows tissue to grow into it, thereby functioning to anchor the device within the patient. Typically, the cuff is placed in the middle section 70. Additionally, referring to FIGS. 14A and 14B, in certain embodiments with two lumens, one lumen 524 extends distally beyond the distal end 75 to the physical end 77 of the conduit 108. At the physical end 77 an opening communicates with the lumen 524. Two holes 69, 69' are located immediately proximal to the distal end 75 which communicate with the lumen 522.

In some embodiments, the catheter has a certain pressure at which it leaks and a certain tensile strength along its length. Leak pressure is determined by clamping the conduit closed at a position which is immediately proximal to the notch and attaching a pressure source to either of the connecting tubes, each of which communicate with one of the lumens through the hub. For each sample, pressure is applied to each connecting tube/lumen in steps of 12 psi, 25 psi, 35 psi, and 45 psi. At each pressure step, the pressure is applied to one connecting tube/lumen for 30 seconds; the pressure source is removed; the pressure source is reattached to the other connecting tube/lumen; and pressure is applied to the other connecting tube/lumen for 30 seconds. Three samples were aged 2½ years ("aged samples") and three samples were non-aged ("non-aged samples").

Tensile strength was determined along the length of a conduit at locations roughly equating with the proximal, middle, and distal sections of the conduit. Tensile strength of the proximal section was determined bib clamping the conduit at about a first point which is approximately one third of a conduit length from the proximal end that couples with the hub and pulling the conduit at that point in a direction opposite from the proximal end to which a fixed clamp is attached. Tensile strength of the middle section was determined by clamping the conduit at about the first point and about a second point which is approximately two thirds of a conduit length from the proximal end and pulling the clamps at those points apart and in opposite directions. Tensile strength of the distal section was determined in a similar manner to the middle section, except the clamps were positioned at about the second point and about the physical end of the conduit. For each section, the tensile strength was determined for three aged samples and three non-aged samples. Results are shown in Table 4, below.

TABLE 4

| | \multicolumn{4}{c}{TENSILE STRENGTH} | | | |
|---|---|---|---|---|
| SECTION | AGED (MEAN LOAD IN POUNDS) | AGED STANDARD DEVIATION | NON-AGED (MEAN LOAD IN POUNDS) | NON-AGED STANDARD DEVIATION |
| PROXIMAL | 31.77 | 1.40 | 30.52 | 0.86 |
| MIDDLE | 28.51 | 0.97 | 26.91 | 0.86 |
| DISTAL | 17.02 | 0.76 | 14.94 | 1.36 |

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method of delivering fluid to a patient, the method comprising:
   placing a catheter within a vessel of the patient, the catheter comprising:
   a hub; and
   a flexible conduit comprising an outer wall and an internal divider defining at least a first and second lumen, the conduit further comprising:
   a cylindrical proximal section;
   a frusto-conical middle section; and
   a cylindrical distal section;
   wherein the frusto-conical middle section includes a transition zone extending from a first point to a second point and having a first cross-sectional area at the first point and a second cross-sectional area at the second point, wherein the first point is proximal of the second point, and wherein the first cross-sectional area is larger than the second cross-sectional area;
   wherein a thickness of the outer wall smoothly increases in a distal to proximal direction over the transition zone with a concomitant increase in cross-sectional area in a distal to proximal direction of each of the first and second lumens over the transition zone;
   at least one connecting tube to the hub, whereby the at least one connecting tube is in communication with at least one of the lumens; and
   wherein the cylindrical proximal section is in direct contact with the hub;
   attaching a fluid source to the at least one connecting tube; and
   delivering fluid to the patient through the at least one connecting tube.

2. The method of claim 1 wherein a surface of the flexible conduit is treated to inhibit association of materials with the conduit.

3. The method of claim 1 wherein a surface of the flexible conduit is treated with heparin.

4. The method of claim 1 wherein the flexible conduit is reinforced to prevent kinking.

5. The method of claim 1 wherein the flexible conduit is reinforced by the change in cross-sectional area along the length of the flexible conduit, without adding a wire to the flexible conduit.

6. The method of claim 1 wherein the first lumen and second lumen are in constant open fluid communication with the hub.

7. The method of claim 6 further comprising at least two connecting tubes connected to and in fluid communication with the hub.

8. The method of claim 7 wherein the hub contains a void that links the first lumen and the second lumen to one of the connecting tubes.

9. The method of claim 1 wherein the cross-section of one end of the first lumen and the second lumen are semi-circular, circular, round, or oval.

10. The method of claim 9 wherein the cross-sectional diameter of the distal most end of the first lumen and the second lumen are smaller than the cross-sectional diameter of the proximal most end of the first lumen and the second lumen.

* * * * *